United States Patent
Dewdney et al.

(10) Patent No.: US 11,883,514 B2
(45) Date of Patent: Jan. 30, 2024

(54) STABLE LOW PH PERSONAL CARE COMPOSITIONS AND METHODS FOR THE SAME

(71) Applicant: COLGATE-PALMOLIVE COMPANY, New York, NY (US)

(72) Inventors: Nadine Dewdney, Union, NJ (US); Christine Boyke, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 178 days.

(21) Appl. No.: 16/671,996

(22) Filed: Nov. 1, 2019

(65) Prior Publication Data
US 2021/0128430 A1     May 6, 2021

(51) Int. Cl.
*A61K 8/37* (2006.01)
*A61K 8/34* (2006.01)
*A61Q 19/00* (2006.01)
*A61K 8/41* (2006.01)
*A61K 8/36* (2006.01)

(52) U.S. Cl.
CPC ............... *A61K 8/37* (2013.01); *A61K 8/345* (2013.01); *A61K 8/36* (2013.01); *A61K 8/416* (2013.01); *A61Q 19/007* (2013.01)

(58) Field of Classification Search
CPC .......... A61K 8/345; A61K 8/36; A61K 8/416; A61K 8/37; A61Q 9/0007
See application file for complete search history.

(56) References Cited

U.S. PATENT DOCUMENTS

| | | | |
|---|---|---|---|
| 6,193,956 B1 | 2/2001 | Liu et al. | |
| 6,488,916 B1* | 12/2002 | Fowler | A61K 8/06 424/59 |
| 7,758,885 B2 | 7/2010 | Myhra | |
| 9,750,668 B2 | 9/2017 | Strauss et al. | |
| 2004/0234592 A1 | 11/2004 | Carlsson | |
| 2006/0116489 A1* | 6/2006 | Lennon | A61K 8/8158 524/588 |
| 2010/0189674 A1 | 7/2010 | Morrison et al. | |
| 2012/0259010 A1* | 10/2012 | Misso | A61Q 19/00 514/547 |
| 2012/0269867 A1* | 10/2012 | Jimenez | A61P 27/16 424/400 |
| 2013/0276810 A1 | 10/2013 | Hoffmann et al. | |
| 2017/0290748 A1 | 10/2017 | Skubsch et al. | |

FOREIGN PATENT DOCUMENTS

| | | |
|---|---|---|
| EP | 1800715 | 6/2007 |
| EP | 2471505 | 7/2012 |
| EP | 3295931 | 3/2018 |
| KR | 20120058846 | 6/2012 |
| WO | WO 2014/163896 | * 10/2014 |
| WO | 2019/048193 | 9/2017 |

OTHER PUBLICATIONS

Delarom, 2014, "Moisturising Body Lotion with Passiflora," Mintel GNPD AN: 2748729.
International Search Report and Written Opinion of the International Searching Authority in International Application No. PCT/US2018/065733, dated Aug. 28, 2019.
Simon et al., 2013, "Interpreting DSC Curves Part I: Dynamic Measurements," Usercom website http://.masontechnology.ie/x/Usercom_11.pdf.
Carrefour—CMI, 2018, "Non Rinsing Nourishing Care", Mintel Database GNPD AN: 5397515.
Coner, 2017, "Firming Buttocks Cream", Mintel Database GNPD AN: 4817371.
Copomon Enterprises, 2017, "PicturePerfect Hair Bond Sealing Masque", Mintel Database GNPD AN: 5157481.
International Search Report and the Written Opinion of the International Searching Authority issued in International Application PCT/US2019/059439 dated Jul. 23, 2020.
Mohiuddin, 2019, "Skin Care Creams: Formulation and Use", Dermatology Clinics & Research, pp. 238-271.
Oriental Aroma, 2014, "Hair Conditioner", Mintel Database GNPD AN: 2388921.

* cited by examiner

*Primary Examiner* — Genevieve S Alley

(57) ABSTRACT

Personal care compositions and methods for preparing the same are disclosed. The personal care composition may include an emulsifying system, one or more emollients, and one or more humectants. The method for preparing the personal care composition may include contacting the emulsifying system, the one or more emollients, and the one or more humectants with one another.

10 Claims, No Drawings

STABLE LOW PH PERSONAL CARE COMPOSITIONS AND METHODS FOR THE SAME

BACKGROUND

Personal care compositions, such as lotions, may often include one or more conventional and/or non-natural ingredients that provide skin conditioning, anti-foaming, and skin protection. Recent consumer perception regarding non-natural ingredients have pushed compositions to more natural formulations including naturally derived ingredients. As such, efforts have been directed to reducing or eliminating non-natural ingredients from personal care compositions to provide improved consumer perception. The removal or replacement of non-natural ingredients, however, has proven to be especially difficult for low pH formulations. For example, the removal or replacement of non-natural ingredients in low pH (e.g., pH of about 4 to about 5) formulations often result in products that exhibit instability or phase separation during aging studies.

What is needed, then, are improved low pH personal care compositions and methods for preparing the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care composition including an emulsifying system, one or more emollients, and one or more humectants.

In at least one implementation, the emulsifying system may include a cationic surfactant. The cationic surfactant may include an esterquat. The esterquat may include one or more of dibehenoylethyl dimonium chloride, dipalmitoylethyl dimonium chloride, distearoylethyl dimonium chloride, ditallowoyl pg-dimonium chloride, dipalmitoylethyl hydroxyethylmonium methosulfate, distearoylethyl hydroxyethylmonium methosulfate, or combinations thereof. The cationic surfactant may be dipalmitoylethyl dimonium chloride.

In at least one implementation, the emulsifying system may include one or more nonionic surfactants. The one or more nonionic surfactants may include cetearyl alcohol, ceteareth-20, cetyl alcohol, stearyl alcohol, or combinations thereof. The cetearyl alcohol and ceteareth-20 may be present in an amount of about 3 weight % to about 5 weight %, based on a total weight of the personal care composition. The cetearyl alcohol and ceteareth-20 may also be present in an amount of about 4 weight %, based on a total weight of the personal care composition. The cetearyl alcohol and ceteareth-20 may further be present in an amount of greater than or equal to about 5 weight %, based on a total weight of the personal care composition. In at least one implementation, the cetyl alcohol is present in an amount of greater than or equal to about 3 weight %, optionally, about 3.5 weight %, based on a total weight of the personal care composition.

In at least one implementation, the one or more emollients may include isopropyl palmitate. The isopropyl palmitate may be present in an amount of greater than or equal to about 1.5 weight %, based on a total weight of the personal care composition.

In at least one implementation, the isopropyl palmitate may be present in an amount of greater than or equal to about 4 weight, based on a total weight of the personal care composition, the cetyl alcohol and the stearyl alcohol may be present in an amount of greater than or equal to about 6.5 weight %, based on a total weight of the personal care composition, and the nonionic surfactants may include cetearyl alcohol and ceteareth-20 in an amount of greater than or equal to about 4 weight %, based on a total weight of the personal care composition.

In at least one implementation, the one or more humectants may include glycerin, caprylyl glycol, or combinations thereof.

In at least one implementation, the personal care composition is substantially free of silicone, silicone compounds, propylene glycol, mineral oil, petrolatum, polyethylene glycol (PEG), or any combination thereof.

In at least one implementation, the personal care composition is substantially free of silicone, silicone compounds, propylene glycol, mineral oil, petrolatum, or any combination thereof.

In at least one implementation, the personal care composition further includes one or more acids. The one or more acids may include lactic acid.

In at least one implementation, the personal care composition may have an acidic pH. For example, the pH may be from about 4 to about 6, or the pH may be from about 4 to about 5.

In at least one implementation, the personal care composition may have a viscosity of greater than or equal to 50,000 centipoise (cP) and less than or equal to 200,000 cP at 25° C.

In at least one implementation, the personal care composition does not exhibit phase separation after exposure to accelerated aging conditions.

The foregoing and/or other aspects and utilities embodied in the present disclosure may be achieved by providing a method for preparing any of the personal care compositions disclosed herein. The method may include contacting the emulsifying system, the one or more emollients, and the one or more humectants with one another.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that stable, low pH personal care compositions may be prepared by providing a primary emulsifier or primary emulsifiers (e.g., cetearyl alcohol and ceteareth-20) in an amount of about 3% to about 5%, about 3.5% to about 4.5%, or about 4%, cetyl alcohol and stearyl alcohol in a total amount of greater than or equal to about 4% or greater than or equal to about 5%, and cetyl alcohol in an amount of about 3.5% or greater.

The present inventors have also surprisingly and unexpectedly discovered that stable personal care compositions having a pH of from about 4 to about 5 may be prepared when isopropyl palmitate is present in an amount of about 1.5% or at least 1.5%.

The present inventors have further surprisingly and unexpectedly discovered that when isopropyl palmitate is present in an amount of about 4% or greater in the personal care composition, then stable personal care compositions having a pH of from about 4 to about 5 may be prepared by providing a total of cetyl alcohol and stearyl alcohol of about 6.5% or greater, and/or an amount of cetearyl alcohol/ceteareth-20 in an amount of about 4% or greater.

Compositions

Compositions disclosed herein may be or include stable, low pH personal care compositions including an emulsifying system including one or more surfactants and/or one or more emulsifiers, one or more emollients, one or more humectants, or any combination thereof. The compositions disclosed herein may be free or substantially free of silicone, silicone compounds, propylene glycol, mineral oil, petrolatum, polyethylene glycol (PEG), or any combination thereof. For example, the composition may include silicone or silicon compounds and be free or substantially free of PEG. In another example, the composition may include PEG and be free or substantially free of silicone, silicone compounds, propylene glycol, mineral oil, petrolatum, or any combination thereof. In another example, the compositions disclosed herein may be or include a skin moisturizing composition, such as a low pH skin moisturizing composition or a low pH lotion or cream, that is free or substantially free of silicone, silicone compounds, propylene glycol, mineral oil, petrolatum, polyethylene glycol (PEG), or any combination thereof.

The personal care compositions disclosed herein may exhibit comparable, enhanced, or relatively greater stability as compared to conventional personal care compositions including silicone, silicone compounds, propylene glycol, mineral oil, petrolatum, polyethylene glycol (PEG), or any combination thereof. For example, the personal care compositions disclosed herein may exhibit no phase separation, relatively stable pH, and/or relatively stable viscosity when exposed to various aging conditions as compared to conventional personal care compositions including any one or more of silicone, silicone compounds, propylene glycol, mineral oil, petrolatum, polyethylene glycol (PEG), or any combination thereof. As used herein, the term or expression "relatively stable" may refer to a property or value that does not change (e.g., increase or decrease) from an original property or value by an amount greater than 0.5%, greater than 1%, greater than 1.5%, greater than 2%, greater than 2.5%, greater than 3%, greater than 3.5%, greater than 4%, greater than 4.5%, greater than 5%, greater than 6%, greater than 7%, greater than 8%, greater than 9%, or greater than 10%. As further described herein, the personal care composition may include an emulsifying system, one or more emollients, one or more humectants, or any combination thereof capable of or configured to provide comparable or enhanced stability to the personal care composition as compared to conventional personal care compositions including any one or more of silicone, silicone compounds, propylene glycol, mineral oil, petrolatum, polyethylene glycol (PEG), or any combination thereof.

As used herein, the term or expression "personal care composition" may refer to a composition for topical application to skin of mammals, especially humans. The personal care composition may generally be a leave-on personal care composition or rinse off personal care composition, and may include any product applied to a human body. The personal care composition is preferably a leave-on personal care composition. The personal care composition may be in any suitable form. Illustrative forms of the personal care composition may be or include, but is not limited to, a liquid, a lotion, a cream, a foam, a scrub, a gel, a soap bar, a toner, applied with an implement or via a face mask, or the like. Illustrative personal care compositions may be or include, but are not limited to, leave-on skin lotions and creams, emulsion, shampoos, conditioners, shower gels, antiperspirants, deodorants, depilatories, lipsticks, foundations, mascara, sunless tanners, sunscreen lotions, or the like.

The personal care composition may include a hydrophobic phase and a hydrophilic phase combined, mixed, contacted, or otherwise emulsified with one another. For example, the personal care composition may be a water-inoil emulsion including a hydrophilic phase dispersed or suspended in a continuous hydrophobic phase. In another example, the personal care composition may be an oil-in-water emulsion including a hydrophobic phase dispersed or suspended in a continuous hydrophilic phase. In a preferred implementation, the personal care composition is an oil-in-water emulsion including a hydrophobic phase suspended in a continuous hydrophilic phase.

The personal care composition may have an acidic pH. For example, the personal care composition may have a pH of from about 3, about 3.5, about 4, or about 4.5 to about 5, about 5.5, about 6, or about 6.5. In another example, the personal care composition may have a pH of less than 7, less than 6.5, less than 6, less than 5.5, less than 5, or less than 4.5. In a preferred implementation, the personal care composition may have a pH of from about 4.0 to about 5.0, or about 4.2 to about 4.8, more preferably about 4.2 to about 4.6.

As used herein, the term or expression "absorbability" may refer to the speed or how quick the personal care composition is absorbed into the skin. The personal care composition may have an absorbability score or value of greater than or equal to about 2.0, as determined by an Small Sensory panel using a standardized methodology and a 0 to 5 point assessment scale, where '0' represented the lowest level (i.e., none or low) and '5' represented the highest value. For example, the personal care composition may have an absorbability score of greater than or equal to about 2.0, greater than or equal to about 2.2, greater than or equal to about 2.4, greater than or equal to about 2.6, greater than or equal to about 2.8, greater than or equal to about 3.0, greater than or equal to about 3.2, greater than or equal to about 3.4, greater than or equal to about 3.6, greater than or equal to about 3.8, greater than or equal to about 4.0, as determined by the Small Sensory panel. In a preferred implementation, the personal care composition has an absorbability score of greater than or equal to about 2.7.

As used herein, the term or expression "whiteness" or "whiteness score" may refer to the amount of white perceived to be visible on skin during application or rubbing. The personal care composition may have a whiteness score or value of less than or equal to about 3.6, as determined by an Small Sensory panel using a standardized methodology and a 0 to 5 point assessment scale, where '0' represented the lowest level (i.e., none or low) and '5' represented the highest value. For example, the personal care composition may have a whiteness score of less than or equal to about 3.6, less than or equal to about 3.4, less than or equal to about 3.2, less than or equal to about 3.0, less than or equal to about 2.8, less than or equal to about 2.6, less than or equal to about 2.4, less than or equal to about 2.2, less than or equal to about 2.0, less than or equal to about 1.8, less than or equal to about 1.6, less than or equal to about 1.5, less than or equal to about 1.4, less than or equal to about 1.3, less than or equal to about 1.2, less than or equal to about 1.1, less than or equal to about 1, as determined by the Small Sensory panel. In a preferred implementation, the personal care composition has a whiteness score of less than or equal to about 2.7.

As used herein, the term or expression "tackiness" or "tackiness score" may refer to the sticky feeling left after application of the personal care composition on surfaces of the skin. The personal care composition may have a tackiness score or value of less than or equal to about 3.0, as determined by an Small Sensory panel using a standardized methodology and a 0 to 5 point assessment scale, where '0' represented the lowest level (i.e., none or low) and '5' represented the highest value. For example, the personal care composition may have a tackiness score of less than or equal to about 3.0, less than or equal to about 2.8, less than or equal to about 2.6, less than or equal to about 2.4, less than or equal to about 2.2, less than or equal to about 2.0, less than or equal to about 1.8, less than or equal to about 1.6, less than or equal to about 1.4, as determined by the Small Sensory panel. In a preferred implementation, the personal care composition has a tackiness score of less than or equal to about 2.0.

As used herein, the term or expression "spreadability" or "spreadability score" may refer to how easily or the ease at which the personal care composition is distributed on surfaces of the skin. The personal care composition may have a spreadability score or value of greater than or equal to about 2.0, as determined by an Small Sensory panel using a standardized methodology and a 0 to 5 point assessment scale, where '0' represented the lowest level (i.e., none or low) and '5' represented the highest value. For example, the personal care composition may have a spreadability score of greater than or equal to about 2.0, greater than or equal to about 2.2, greater than or equal to about 2.4, greater than or equal to about 2.6, greater than or equal to about 2.8, greater than or equal to about 3.0, greater than or equal to about 3.2, greater than or equal to about 3.4, greater than or equal to about 3.6, greater than or equal to about 3.8, greater than or equal to about 4.0, greater than or equal to about 4.1, greater than or equal to about 4.2, greater than or equal to about 4.3, or greater than or equal to about 4.4, as determined by the Small Sensory panel. In a preferred implementation, the personal care composition has a spreadability score of greater than or equal to about 3.0.

As used herein, the term or expression "greasiness" or "greasiness score" may refer to the amount of greasiness felt on surfaces of the skin during and/or after application. The personal care composition may have a greasiness score or value of less than or equal to about 3.6, as determined by an Small Sensory panel using a standardized methodology and a 0 to 5 point assessment scale, where '0' represented the lowest level (i.e., none or low) and '5' represented the highest value. For example, the personal care composition may have a greasiness score of less than or equal to about 3.6, less than or equal to about 3.4, less than or equal to about 3.2, less than or equal to about 3.0, less than or equal to about 2.8, less than or equal to about 2.6, less than or equal to about 2.4, less than or equal to about 2.2, less than or equal to about 2.0, less than or equal to about 1.8, less than or equal to about 1.7, less than or equal to about 1.6, less than or equal to about 1.5, or less than or equal to about 1.4, as determined by the Small Sensory panel. In a preferred implementation, the personal care composition has a greasiness score of less than or equal to about 2.5.

The personal care composition may have a viscosity, as determined using a viscometer at a temperature of about 25° C., of greater than or equal to about 5,000 centipoise (cP), about 10,000 cP, or about 20,000 cP and/or less than or equal to about 200,000 cP, as measured with a T93 spindle at about 10 RPM for viscosities of up to about 100,000 cP, or as measured with a T95 spindle at about 5 RPM for viscosities of from about 100,000 cP to about 200,000 cP. As used herein, the term "viscosity" may refer to the internal resistance to flow exhibited by a fluid or the ratio of shearing stress to rate of shear, and may be measured in poise or centipoises (cP). For example, the personal care composition may have a viscosity of greater than or equal to about 5,000 cP, greater than or equal to about 10,000 cP, greater than or equal to about 20,000 cP, greater than or equal to about 25,000 cP, greater than or equal to about 30,000 cP, greater than or equal to about 35,000 cP, greater than or equal to about 40,000 cP, greater than or equal to about 45,000 cP, greater than or equal to about 60,000 cP, greater than or equal to about 70,000 cP, greater than or equal to about 100,000 cP at about 25° C. In another example, the personal care composition may have a viscosity of less than or equal to about 200,000 cP, less than or equal to about 150,000 cP, less than or equal to about 100,000 cP, less than or equal to about 95,000 cP, less than or equal to about 90,000 cP, less than or equal to about 85,000 cP, less than or equal to about 80,000 cP, less than or equal to about 75,000 cP, less than or equal to about 70,000 cP, less than or equal to about 65,000 cP, less than or equal to about 60,000 cP, or less than or equal to about 55,000 cP, at about 25° C. In a preferred implementation, the personal care composition has a viscosity of from about 50,000 cP to about 150,000 cP, at about 25° C.

The personal care compositions disclosed herein may not exhibit any phase separation after exposure to accelerated aging conditions. The personal care compositions disclosed herein may not exhibit any phase separation after exposing the personal care composition to one or more freeze-thaw treatments. For example, the personal care composition disclosed herein may not exhibit any phase separation after freeze-thawing treatment between −30° C. and room temperature for at least or about 3 cycles/treatments. In another example, the personal care composition disclosed herein may not exhibit any phase separation after freeze-thawing treatment between −10° C. and room temperature for at least or about 3 cycles/treatments.

The personal care composition disclosed herein may not exhibit any phase separation after exposing the personal care composition to temperatures of about 30° C., about 40° C., or about 49° C., for extended periods of time. For example, the personal care composition disclosed herein may not exhibit any phase separation after maintaining the personal care composition at about 49° C. for at least 4 weeks or more. In another example, the personal care composition disclosed herein may not exhibit any phase separation after maintaining the personal care composition at about 30° C. for at least 4 weeks, at least 8 weeks, or at least 13 weeks, or more. In yet another example, the personal care composition disclosed herein may not exhibit any phase separation after maintaining the personal care composition at about 40° C. for at least 4 weeks, at least 8 weeks, or at least 13 weeks, or more. It should be appreciated that phase separation in the personal care composition is determined visually.

In an exemplary implementation, the personal care composition may be free or substantially free of any one or more of silicone, silicone compounds, propylene glycol, mineral oil, petrolatum, polyethylene glycol (PEG), or any combination thereof. For example, the personal care composition may include polyethylene glycol (PEG) and may be free or substantially free of silicone, silicone compounds, propylene glycol, mineral oil, and petrolatum. In another example, the personal care composition may exclude all of the following: silicone, silicone compounds, propylene glycol, mineral oil, petrolatum, and polyethylene glycol (PEG). In yet another example, the personal care composition may only include one, two, three, four, or five of the following and exclude the remaining: silicone, silicone compounds, propylene glycol, mineral oil, petrolatum, and polyethylene glycol (PEG). Illustrative silicone or silicone compounds may be or include, but are not limited to, polysiloxane polymers, such as dimethicone, dimethiconol, cyclopentasiloxane, or any combination thereof.

In at least one implementation, the personal care composition may include one or more humectants. Illustrative humectants may be or include, but are not limited to, glycerin (e.g., vegetable refined glycerin, etc.), propylene glycol, polyethylene glycol, ascorbic acid, ascorbyl dipalmitate, acetamide MEA, caprylyl glycol, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, or the like, or combinations thereof. In a preferred implementation, the humectants may be or include, but is not limited to, glycerin, caprylyl glycol, or combinations thereof.

The one or more humectants may be present in an amount of from about 0.1 weight % to about 10 weight % or from about 0.5 weight % to about 20 weight %, based on a total weight of the personal care composition. For example, any one or more of the humectants may be present in an amount of from about 0.1 weight %, about 0.2 weight %, about 0.3 weight %, about 0.4 weight %, about 0.5 weight %, about 1 weight %, about 1.5 weight %, about 2 weight %, about 2.5 weight %, about 3 weight %, about 3.5 weight %, about 4 weight %, about 4.5 weight %, or about 5 weight % to about 5.5 weight %, about 6 weight %, about 6.5 weight %, about 7 weight %, about 7.5 weight %, about 8 weight %, about 8.5 weight %, about 9 weight %, about 9.5 weight %, about 10 weight %, or about 20 weight %, based on a total weight of the personal care composition. In a preferred implementation, the humectant includes glycerin and/or caprylyl glycol in an amount of from about 1.5 to about 10 weight %, about 2 weight % to about 8 weight %, about 3 weight % to about 7 weight %, or about 5 weight %, based on a total weight of the personal care composition.

In at least one implementation, the personal care composition may include one or more preservatives in an amount of greater than 0 weight % and less than or equal to about 3 weight %, less than or equal to about 2.5 weight %, less than or equal to about 2 weight %, less than or equal to about 1.5 weight %, less than or equal to about 1 weight %, less than or equal to about 0.75 weight %, less than or equal to about 0.5 weight %, or less than or equal to about 0.25 weight %, based on a total weight of the personal care composition. Illustrative preservatives may include, but are not limited to, benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5, 5-dimethyl hydantoin; formaldehyde; iodopropynl butyl carbamate, butyl paraben; ethyl paraben; methyl paraben; propyl paraben, mixture of methyl isothiazolinone/methylchloroisothiazoline in a 1:3 wt. ratio; mixture of polyvinylpyrro/butyl paraben/methyl paraben/propylparaben; 2-phenoxyethanol; tris-hydroxyethyl-hexahydrotriaz-ine; methylisothiazolinone; 5-chloro-2-methyl-4-isothiazolin-3-one; 1,2-dibromo-2,4-dicyanobutane; 1-(3-chloroalkyl)-3,5, 7-triaza-azoniaadam-antane chloride; sodium benzoate; organic acids, sorbic acid, lactic acid, citric acid, or the like, or any combination thereof.

In at least one implementation, the one or more preservatives include sodium benzoate in an amount of from greater than 0 weight % to less than or equal to 2 weight %, greater than 0 weight % to less than or equal to 1 weight %, or about 0.5 weight %, based on a total weight of the personal care composition. In yet another implementation, the preservative includes sodium benzoate in an amount of from greater than 0 weight % to less than or equal to 2 weight %, greater than 0 weight % to less than or equal to 1 weight %, or greater than 0 weight % to less than or equal to 0.8 weight %, based on a total weight of the personal care composition. For example, the personal care composition may include sodium benzoate in an amount of about 0.3 weight %, based on a total weight of the personal care composition. In at least one implementation, the personal care compositions and/or the preservative system thereof may be free or substantially free of phenoxyethanol.

In at least one implementation, the personal care composition may include one or more acids, one or more bases, and/or one or more buffers configured to adjust or control the pH of the personal care composition. The one or more acids, one or more bases, and/or one or more buffers may, separately and independently, be present in an amount of from greater than 0 weight % to less than or equal to about 5 weight %, less than or equal to about 4 weight %, less than or equal to about 3 weight %, less than or equal to about 2 weight %, less than or equal to about 1 weight %, less than or equal to about 0.75 weight %, less than or equal to about 0.5 weight %, less than or equal to about 0.4 weight %, or less than or equal to about 0.35 weight %, based on a total weight of the personal care composition or the hydrophilic phase thereof. Illustrative bases may include, but are not limited to, ammonia; mono-, di-, and tri-alkyl amines; mono-, di-, and tri-alkanolamines; alkali metal and alkaline earth metal hydroxides; sodium hydroxide, potassium hydroxide, lithium hydroxide, monoethanolamine, triethylamine, isopropanolamine, diethanolamine, triethanolamine, or the like, or combinations thereof. Illustrative acids may include, but are not limited to, mineral acids, such as hydrochloric acid, nitric acid, phosphoic acid, and sulfuric acid, organic acids, polycarboxylic acids, such as citric acid, glycolic acid, and lactic acid, or the like, or combinations thereof. In a preferred implementation, the hydrophilic phase includes at least one acid, such as lactic acid, and the lactic acid is present in an amount of from greater than 0 weight % to about 0.8 weight %, from about 0.4 weight % to about 0.8 weight %, or about 0.65 weight %, based on a total weight of the personal care composition.

The personal care composition may include an emulsifying system including one or more surfactants and/or one or more emulsifiers. The one or more surfactants and/or the one or more emulsifiers may be at least partially configured to provide enhanced or relatively greater stability to the personal care composition, as compared to conventional personal care compositions. The one or more surfactants and/or emulsifiers may include, but are not limited to, one or more anionic surfactants, one or more cationic surfactants, one or more zwitterionic surfactants, one or more nonionic surfactants, or mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference to the extent consistent with the present disclosure.

Illustrative anionic surfactants may include, but are not limited to, stearic acid, water-soluble salts of higher fatty acid monoglyceride monosulfates, such as a sodium salt of a monosulfated monoglyceride of hydrogenated coconut oil fatty acids, such as sodium N-methyl N-cocoyl polyviny, sodium cocomonoglyceride sulfate. Illustrative anionic surfactants may also include higher alkyl sulfates. As used herein, "higher alkyl" refers to $C_{6-30}$ alkyls. For example, the anionic surfactant may be or include sodium lauryl sulfate. The anionic surfactants may also include higher alkyl-ether sulfates. In another implementation, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary implementation, the anionic surfactant may be or include a water soluble salt of alkyl sulfates having from 10 to 18 carbon atoms in the alkyl radical and water soluble salts of sulfonated monoglycerides of fatty acids having from 10 to 18 carbon atoms.

Illustrative cationic surfactants may be or include, but are not limited to, ammonium salts such as distearyldimethylammonium chloride, halide salts of methylated ammonium wherein at least one and preferably two or three of the groups on the nitrogen are long chain substantially saturated material such as tallow fatty radicals, hydrogenated tallow fatty radicals, methosulfate anionic salts of the above, long chain amidoderivative such as mink oil amidopropyldimethyl-2-hydroxyethylammonium chloride (Quaternium 26), aromatics such as isododecylbenzyl triethanol ammonium chloride, N-alkylated amphoteric materials such as N-alkylated betaines, alkylamines, alkylimidazolines, various ethoxylated amines, Quaternium-8, -14, -18, -24, -26, -27, -33, -43, -52, -53, -60, -62, -83, esterquats, or the like, or any combination thereof. Illustrative esterquats may be or include, but are not limited to, dibehenoylethyl dimonium chloride, dipalmitoylethyl dimonium chloride, distearoylethyl dimonium chloride, ditallowoyl pg-dimonium chloride, dipalmitoylethyl hydroxyethylmonium methosulfate, distearoylethyl hydroxyethylmonium methosulfate, or the like, or combinations and mixtures thereof. In a preferred implementation, the personal care composition includes one or more cationic surfactants and the cationic surfactants include dipalmitoylethyl dimonium chloride.

Illustrative nonionic surfactants may be or include, but are not limited to, higher alcohols or fatty alcohols, including straight chain alcohols or ethoxylates thereof, sorbitan fatty acid esters (e.g., sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate, etc.); glycerin polyglycerin aliphatic acids (e.g., mono cottonseed oil fatty acid glycerin, glyceryl monoerucate, glycerin sesquioleate, glyceryl monostearate, glyceryl stearate, α, α'-glycerin oleate pyroglutamate, monostearate glycerin malic acid, etc.); propylene glycol fatty acid esters (e.g., propylene glycol monostearatem, etc.); hydrogenated castor oil derivatives; glycerin alkylethers, or the like, or combinations thereof. Illustrative nonionic surfactants may also be or include, but are not limited to, sorbitan esters and ethoxylated sorbitan esters (e.g., PEG-20 sorbitan isostearate, sorbitan monolaurate, polysorbate-20, polysorbate-40, polysorbate-60, polysorbate-80); ethoxylates (e.g., Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, etc.); ethoxylated adducts (e.g., PEG-25 stearate, glyceryl stearate, PEG-100 stearate, etc.); polyoxyethylene (100) monostearate, a polyethylene glycol ester of stearic acid, PEG esters (e.g., PEG-8 oleate, PEG-8 laurate, PEG-8 dilaurate, PEG-12 dilaurate, PEG-80 diisostearate, PEG-40 stearate, etc.); propoxylates (e.g., PPG-10 butanediol, PPG-50 oleyl ether, PPG-2-ceteareth-9, PPG-3-deceth-3, PPG-5-ceteth-20); ethoxylated modified triglycerides (e.g., PEG-20 corn glycerides, PEG-12 palm kernel glycerides); alkylphenol aromatic ethoxylates (e.g., dinonylphenol ethoxylate with 9 moles of EO octylphenol ethoxylate with 20 moles of EO, octylphenol ethoxylate with 40 moles of EO); block copolymers that are alkoxylated glycols having ethoxylated and propoxylated segments (e.g., POLOXAMER™ 182 and 234, POLOXAMER™ 105 Benzoate, and MEROXAPOL™ 174); or the like, or combinations thereof. Illustrative ethoxylates may be or include, but are not limited to, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10.

Illustrative nonionic surfactants may also include, but are not limited to, the reaction products of aliphatic alcohols or alkylphenols having 6 to 20 carbon atoms in a linear or branched alkyl chain with ethylene oxide and/or propylene oxide where the alkylene oxide may be from about 6 moles to about 60 moles per mole of alcohol. For example, the nonionic surfactants may include, but are not limited to, alkylamine oxides, mono- and dialkylalkanolamides, fatty acid esters of polyethylenenglycols, ethoxylated fatty acids amides, saturated fatty acid alcohols reacted with ethylene oxide, alkyl polyglycosides, and sorbitan ether esters, one or more Ceteareth-n, such as Ceteareth-2, Ceteareth-3, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, or the like, or combinations thereof, or one or more Ceteareth in combination with a fatty acid alcohol such as stearyl alcohol, oleyl alcohol, linoleyl alcohol, arachidyl alcohol, cetyl alcohol, cetearyl alcohol (i.e., a mixture of cetyl and stearyl alcohols), or the like, or any combination thereof. It should be appreciated that Ceteareth-n is a name of an INCI family and refers to polyoxyethylene ethers of a mixture of high molecular mass saturated fatty alcohols, where the 'n' indicates the average number of ethylene oxide residues in the polyoxyethylene chain. In an exemplary implementation, the nonionic surfactants include cetearyl alcohol, ceteareth-20, cetyl alcohol, stearyl alcohol, or combinations thereof. It should be appreciated that Ceteareth-20 (CAS Number 68439-49-6) is a polyethylene glycol ether of cetearyl alcohol.

The nonionic surfactants may include one or more fatty alcohols or higher alcohols. Illustrative fatty alcohols or higher alcohols may be or include, but are not limited to, straight chain alcohols, such as a $C_{12-22}$ fatty alcohol, or preferably a $C_{16-18}$ fatty alcohol, lauryl alcohol, myristyl alcohol, cetyl alcohol, behenyl alcohol, stearyl alcohol, cetyl-stearyl alcohol 50/50, or the like, or combinations thereof. Illustrative fatty alcohols may also include branch chain alcohols, such as monostearyl glycerin ether (batyl alcohol), 2-decyltetradecynol, lanolin alcohol, cholesterol, phytosterol, hexyl dodecanol, isostearyl alcohol, octyl dodecanol), or the like, or combinations thereof. In a preferred implementation, the personal care composition or the emulsifying system thereof includes cetearyl alcohol, ceteareth-20, cetyl alcohol, stearyl alcohol.

The amount of each of the one or more surfactants and/or emulsifiers present in the personal care composition or the emulsifying system thereof may vary widely. For example, each of the one or more surfactants and/or emulsifiers may, separately and independently, be present in an amount of from about greater than 0 weight % to less than or equal to about 20 weight %, based on a total weight of the personal care composition or the emulsifying system thereof. For example, each of the one or more surfactants and/or emulsifiers may, separately and independently, be present in an amount of from about greater than 0 weight %, 0.25 weight %, about 0.5 weight %, about 0.75 weight %, about 1 weight %, about 1.25 weight %, about 1.5 weight %, about 1.75 weight %, about 2 weight %, about 2.25 weight %, about 2.5 weight %, or about 3 weight % to about 3.5 weight %, about 4 weight %, about 4.5 weight %, about 5 weight %, about 5.5 weight %, about 6 weight %, or greater, based on a total weight of the personal care composition or the emulsifying system thereof. In another example, each of the one or more surfactants and/or emulsifiers may, separately and independently, be present in an amount of from about greater than 0 weight %, about 1 weight %, about 2 weight %, about 3 weight %, about 4 weight %, about 5 weight %, about 6 weight %, or about 7 weight % to about 8 weight %, about 9 weight %, about 10 weight %, about 11 weight %, about 12 weight %, about 13 weight %, about 14 weight %, about 15 weight %, or about 20 weight %, based on a total weight of the personal care composition or the emulsifying system thereof.

In at least one implementation, a weight ratio of any one surfactant or emulsifier to any other surfactant or emulsifier in the emulsifying system may vary from about 0.1:1 to about 3:1. For example, the weight ratio of any one surfactant/emulsifier to any other surfactant/emulsifier in the emulsifying system may be from about 0.1:1, about 0.2:2, about 0.3:1, about 0.4:1, about 0.5:1, about 0.6:1, about 0.7:1, about 0.8:1, or about 0.9:1 to about 1:1, about 1.1:1, about 1.2:1, about 1.3:1, about 1.4:1, about 1.5:1, about 2:1, about 2.5:1, or about 3:1.

In at least one implementation, a weight ratio of any one or more of the emulsifiers to any one or more of the stabilizers may be from about 1:1 to about 1.5:1. For example, a weight ratio of ceteareth-20 and cetearyl alcohol to cetyl and/or stearyl alcohol may be from about 1:1 to about 1.5:1. In another implementation, a weight ratio of any one or more of the stabilizers to any one or more of the emollients may be from about 1:1 to about 3:1.

The personal care compositions disclosed herein may include one or more emollients. The one or more emollients may be configured to maintain a soft, smooth, and pliable appearance to the skin The one or more emollients may be or include, but are not limited to, fatty esters, fatty alcohols, or combinations thereof. Illustrative emollients may be or include, but are not limited to, diisopropyl adipate, oleyl alcohol, lanolin, isopropyl myristate, isopropyl palmitate, coco-caprylate, diethylhexyl carbonate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, polyoxypropylene (5) poloxyethylene (20) cetyl ether (PPG-5-Ceteth-20), 2-ethylhexyl isononoate, 2-ethylhexyl stearate, $C_{12}$ to $C_{16}$ fatty alcohol, $C_{12}$ to $C_{16}$ fatty alcohol lactate, isopropyl lanolate, 2-ethyl-hexyl salicylate, or the like, or combinations thereof. In some implementations, the one or more emollients may be a combination of fatty alcohols. In some implementations, the one or more emollients may be 1-hexadecanol, acetylated lanolin, behenocyl dimethicone, $C_{12-15}$ alkyl benzoate, cetearyl octanoate, cocoglycerides, dicaprylate/dicaprate dimethicone copolyol, dimethiconol, dioctyl adipate, glyceryl stearate, isocetyl alcohol, isohexadecane, isopentylcyclohexanone, isopropyl palmitate, lauryllactate, mineral oil, methoxy peg-22/dodecyl glycol copolymer, myristyl lactate, ocryldodecyl neopentanoate, octyl cocoate, octyl palmitate, octyl stearate, octyldodecyl neopentanoate, polyglyceryl-4 isosterate, polyoxyl 40 stearate, polyoxymethylene urea, potassium sorbate, propylene glycol, propylene glycol isoceth-3 acetate, propylene glycol myristyl ether acetate, or combinations thereof. Illustrative emollients may also include, but are not limited to, a high molecular weight saturated and unsaturated fatty alcohol such as, but not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, or the like, or any combination thereof. As discussed above, in at least one implementation, the personal care composition may be free or substantially free of silicone and/or silicone compounds. As such, the personal care composition may be free or substantially free of behenocyl dimethicone, dicaprylate/dicaprate dimethicone copolyol, dimethiconol, or the like.

In a preferred implementation, the emollient may be selected from isopropyl palmitate, coco-caprylate, cocoglyceride, diethylhexyl carbonate, or a combination thereof.

In at least one implementation, the personal care compositions disclosed herein may include one or more emollients in an amount from greater than 0 weight % to about 5 weight %, based on a total weight of the personal care composition. For example, the one or more emollients may be present in an amount of from greater than 0 weight %, about 0.1 weight %, about 0.3 weight %, about 0.5 weight %, about 1 weight %, or about 2 weight % to about 2.5 weight %, about 3 weight %, about 3.5 weight %, about 4 weight %, or about 5 weight %, based on a total weight of the personal care composition.

In at least one implementation, the emollient system may include one or more stabilizers. The one or more stabilizers may be or include, but are not limited to cetyl alcohol, stearyl alcohol, or combinations thereof. The one or more stabilizers may be present in an amount of from greater than 0 weight % to about 5 weight %, based on a total weight of the personal care composition. For example, the one or more stabilizers may be present in an amount of from greater than 0 weight %, about 0.1 weight %, about 0.3 weight %, about 0.5 weight %, about 1 weight %, or about 2 weight % to about 2.5 weight %, about 3 weight %, about 3.5 weight %, about 4 weight %, or about 5 weight %, based on a total weight of the personal care composition.

In a preferred implementation, the personal care composition or the emulsifying system thereof may include a combination of dipalmitoylethyl dimonium chloride, cetearyl alcohol/ceteareth-20, stearyl alcohol, cetyl alcohol, isopropyl palmiate, or combinations thereof.

In some implementation, the personal care composition may include one or more skin care agents. Any suitable skin care agents that do not adversely affect the stability and/or efficacy of the personal care composition may be utilized. The skin care agents may generally include one or more polymers (e.g., polyvinylpyrrolidone), starches (e.g., tapioca starches, hydrophobically modified corn starch, such as DRY-FLO TS® CAS Nos. 68989-12-8, 68554-70-1, 9005-25-8, etc.), protein derivatives (e.g., derivatized hydrolyzed wheat protein), ethoxylated fatty ethers, cellulosics (e.g., hydroxyethylcellulose), or the like, or combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred implementation, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glyceroth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, or the like, or combinations thereof. In a preferred implementation, the skin care agent is or includes a conditioner, such as a cationic cellulose polymer (e.g., polyquaternium-7). As indicated above, the personal care composition may be free or substantially free of any one or more of PEG, mineral oil, and petrolatum. Accordingly, the personal care composition or the other skin care agents thereof may not include PEG, mineral oil, and/or petrolatum.

The personal care composition may include one or more additional optional ingredients. Illustrative optional ingredients may include, but are not limited to, one or more dyes, fragrances, preservatives, thickeners, viscosity modifiers, antioxidants, chelating agents (e.g., EDTA, phosphates, etc.), opacifiers, hydric solvents, hydrotropes, antimicrobials, or the like, or any combination thereof. In at least one implementation, the personal care composition may be free or substantially free of parabens.

The personal care composition may include water. The water may be deionized water, demineralized water, and/or softened water. Water may make up the balance of the personal care composition. For example, the amount of water present in the personal care composition may be greater than 60 weight %, greater than 65 weight %, greater than 70 weight %, greater than 75 weight %, greater than 80 weight %, greater than 85 weight %, greater than 90 weight %, greater than 92 weight %, greater than 94 weight %, greater than 96 weight %, or more, based on a total weight of the personal care composition. The amount of water in the personal care composition may include free water added and water introduced with other components or materials of the personal care composition. For example, the amount of the water in the personal care composition may include free water and water associated with one or more surfactants and/or any other components of the personal care composition.

Methods

The present disclosure may provide methods for preparing stable personal care compositions. Particularly, the present disclosure may provide methods for preparing stable, low pH personal care compositions that are free or substantially free of silicone, silicone compounds, propylene glycol, mineral oil, petrolatum, polyethylene glycol (PEG), or any combination thereof. The present disclosure may also provide methods for preventing the separation of hydrophobic and hydrophilic phases in personal care compositions that are free or substantially free of silicone, silicone compounds, propylene glycol, mineral oil, petrolatum, polyethylene glycol (PEG), or any combination thereof when exposed to various aging conditions. It should be appreciated by one having ordinary skill in the art that the aging conditions may be provided or defined by the International Council for Harmonisation of Technical Requirements for Pharmaceuticals for Human Use (ICH) Guidelines. The method may include mixing, combining, stirring, emulsifying, or otherwise contacting two or more of the components/ingredients disclosed herein with one another. The method may also include heating the components/ingredients before, during, or after mixing, combining, stirring, emulsifying, or otherwise contacting the components with one another. The method may include preparing a hydrophobic phase and a hydrophilic phase, and contacting the hydrophobic phase with the hydrophilic phase. For example, the method may include preparing the hydrophobic phase including one or more of the components disclosed herein, preparing the hydrophilic phase including one or more of the components disclosed herein, and mixing, combining, stirring, emulsifying, or otherwise contacting the hydrophobic phase and the hydrophilic phase with one another. The method may also include heating the hydrophilic phase and/or the hydrophobic phase while mixing, combining, stirring, emulsifying, or otherwise contacting the hydrophobic phase and the hydrophilic phase with one another. The hydrophobic phase and/or the hydrophilic phase may be heated at a temperature of from about 60° C. to about 90° C., about 65° C. to about 85° C., about 70° C. to about 80° C., or about 75° C. to about 80° C.

The method for preparing stable personal care compositions may also include preparing an emulsifying system including one or more surfactants and/or emulsifiers to enhance the stability of the personal care composition. The method of preparing the emulsifying system may include mixing, combining, stirring, or otherwise contacting the one or more surfactants and/or emulsifiers with one another. For example, the method of preparing the emulsifying system may include mixing, combining, stirring, or otherwise contacting dipalmitoylethyl dimonium chloride, cetearyl alcohol and ceteareth-20, stearyl alcohol, isopropyl palmitate, cetyl alcohol, or any combination thereof with one another.

All ingredients for use in the compositions described herein should be topically acceptable. As used herein, "topically acceptable" may refer any ingredient that is present in a composition as described in an amount and form which does not render the composition unsafe for use on surfaces of skin.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Test personal care compositions (1)-(17) were prepared by combining the ingredients/components according to Tables 1A and 1B. Particularly, the amount of dipalmitoylethyl dimonium chloride, cetearyl alcohol and ceteareth-20, stearyl alcohol, and cetyl alcohol were combined according to Tables 1A and 1B, and the remaining components were combined according to the ranges as provided in Table 1C. Generally, the ingredients/components of each of the test personal care compositions (1)-(17) were combined according to the ranges disclosed in Table 1D. As indicated in Tables 1A and 1B, it should be appreciated that the amount of dipalitoylethyl dimonium chloride was generally present in an amount of from about 0.3% to about 0.5%, and that all remaining raw materials were generally held constant with the exception of water, which was adjusted to accommodate the variances in the amount of cetearyl alcohol/ceteareth-20, stearyl alcohol, cetyl alcohol, isopropyl palmitate, or combinations thereof.

TABLE 1A

| Personal Care Compositions (1)-(8) Weight (%) | | | | | | | | |
|---|---|---|---|---|---|---|---|---|
| COMPONENT | 1 | 2 | 3 | 4 | 5 | 6 | 7 | 8 |
| Dipalmitoylethyl Dimonium Chloride | 0.50 | 0.30 | 0.30 | 0.50 | 0.30 | 0.50 | 0.30 | 0.30 |
| Cetearyl Alcohol/ Ceteareth-20 | 2.00 | 4.00 | 4.00 | 4.00 | 4.00 | 2.00 | 2.00 | 2.00 |
| Stearyl Alcohol | 1.50 | 3.00 | 3.00 | 3.00 | 1.50 | 3.00 | 1.50 | 1.50 |
| Cetyl Alcohol | 3.50 | 1.50 | 3.50 | 1.50 | 3.50 | 1.50 | 1.50 | 3.50 |
| Isopropyl Palmitate | 4.00 | 4.00 | 1.50 | 1.50 | 4.00 | 4.00 | 4.00 | 1.50 |

TABLE 1B

Personal Care Compositions (9)-(17)
Weight (%)

| COMPONENT | 9 | 10 | 11 | 12 | 13 | 14 | 15 | 16 | 17 |
|---|---|---|---|---|---|---|---|---|---|
| Dipalmitoylethyl Dimonium Chloride | 0.50 | 0.30 | 0.50 | 0.50 | 0.50 | 0.30 | 0.30 | 0.40 | 0.50 |
| Cetearyl Alcohol/ Ceteareth-20 | 2.00 | 2.00 | 4.00 | 2.00 | 4.00 | 2.00 | 4.00 | 3.00 | 4.00 |
| Stearyl Alcohol | 3.00 | 3.00 | 1.50 | 1.50 | 1.50 | 3.00 | 1.50 | 2.25 | 3.00 |
| Cetyl Alcohol | 3.50 | 1.50 | 3.50 | 1.50 | 1.50 | 3.50 | 1.50 | 2.50 | 3.50 |
| Isopropyl Palmitate | 1.50 | 1.50 | 1.50 | 1.50 | 4.00 | 4.00 | 1.50 | 2.75 | 4.00 |

TABLE 1C

Remaining Components of Personal Care Compositions (1)-(17)

| COMPONENT | Range |
|---|---|
| Deionized Water | 72-80 |
| Caprylyl Glycol | 0.1-3 |
| Preservative | 0.1-3 |
| Acid | 0.1-2 |
| Glycerin | 1-6 |
| Amino Acids | 0.1-4 |
| Cocoglycerides | 1-4 |
| Coco-caprylate | 1-4 |
| Diethylhexyl Carbonate | 0.1-3 |

TABLE 1D

Amount of Components in Personal Care Compositions (1)-(17)

| COMPONENT | Range |
|---|---|
| Water | QS |
| Humectants | 1-6 |
| Preservatives | 0.5-1.5 |
| Cationic Surfactants | 0.1-2 |
| Nonionic Surfactants | 2-4 |
| Fatty Alcohols | 0.5-4 |
| Emollient/Skin conditioning agent | 0.1-5 |

Example 2

The stability of each of the test personal care compositions (1)-(17) prepared in Example 1 was evaluated. Particularly, the stability of each of the test personal care compositions (1)-(17) of Example 1 was evaluated by measuring or observing the pH and viscosity under various accelerated aging conditions.

To evaluate the viscosity under the various accelerated aging conditions, each of the test personal care compositions (1)-(17) was placed in a respective glass jar and exposed to an environment maintained at the particular conditions (e.g., time and temperature) indicated in Table 2. After the respective times of each of the studies elapsed, each of the personal care compositions was removed from the environment and allowed to cool in a monitored stability chamber maintained at about 25° C. After cooling to about 25° C., the viscosity and pH were measured, and the personal care compositions were observed/evaluated visually. Viscosity was measured using a Brookfield rheometer with spindle T-93 at 10 RPM for about 1 minute.

The results of the pH and viscosity stability analysis of the test personal care compositions (1)-(17) are summarized in Tables 2 and 3, respectively. It should be appreciated that the personal care composition was considered relatively stable if no separation was observed and the viscosity and pH values were deemed relatively stable throughout the analysis, based on the definition of "relatively stable" disclosed herein.

TABLE 2 pH of Control and Test Personal Care Compositions (C) and (1)-(17) [A]

| # | Initial | −30° C. [B] F-T (×3) | −10° C. [C] F-T (×3) | 49° C. 4 wks | 30° C. 4 wks | 30° C. 8 wks | 30° C. 13 wks | 40° C. 4 wks | 40° C. 8 wks | 40° C. 13 wks |
|---|---|---|---|---|---|---|---|---|---|---|
| 1 | 4.3 | 4.32 | 4.32 | Sep. | 4.29 | 4.25 | 4.26 | 4.25 | 4.2 | 4.24 |
| 2 | 4.38 | 4.38 | 4.38 | Sep. | 4.36 | 4.33 | 4.33 | 4.24 | 4.27 | 4.28 |
| 3 | 4.23 | 4.27 | 4.26 | 4.17 | 4.24 | 4.2 | 4.2 | 4.15 | 4.17 | 4.18 |
| 4 | 4.3 | Sep. | 4.31 | 4.25 | 4.26 | 4.23 | 4.24 | 4.18 | 4.18 | 4.21 |
| 5 | 4.34 | 4.35 | 4.36 | Sep. | 4.34 | 4.29 | 4.3 | 4.24 | 4.24 | 4.28 |
| 6 | 4.35 | Sep. | 4.33 | Sep. | 4.34 | 4.29 | 4.29 | 4.23 | 4.4 | 4.24 |
| 7 | 4.32 | Sep. | Sep. | Sep. | 4.33 | 4.28 | 4.29 | Sep. | Sep. | Sep. |
| 8 | 4.34 | Sep. | 4.34 | Sep. | 4.3 | 4.27 | 4.27 | 4.21 | 4.22 | 4.22 |
| 9 | 4.38 | 4.39 | 4.42 | Sep. | 4.35 | 4.31 | 4.31 | 4.24 | 4.25 | 4.31 |
| 10 | 4.26 | 4.29 | 4.31 | Sep. | 4.27 | 4.24 | 4.24 | 4.18 | 4.19 | 4.18 |
| 11 | 4.37 | 4.39 | 4.38 | 4.28 | 4.37 | 4.33 | 4.33 | 4.27 | 4.28 | 4.28 |
| 12 | 4.21 | 4.24 | 4.24 | Sep. | 4.21 | 4.2 | 4.2 | 4.15 | 4.14 | 4.15 |
| 13 | 4.33 | 4.33 | 4.34 | Sep. | 4.31 | 4.27 | 4.27 | 4.22 | 4.22 | 4.24 |
| 14 | 4.38 | Sep. | 4.38 | Sep. | 4.35 | 4.32 | 4.29 | 4.25 | 4.24 | 4.3 |
| 15 | 4.3 | 4.29 | 4.31 | Sep. | 4.28 | 4.26 | 4.25 | 4.2 | 4.2 | 4.23 |
| 16 | 4.29 | 4.32 | 4.31 | Sep. | 4.27 | 4.24 | 4.26 | 4.2 | 4.19 | 4.22 |
| 17 | 4.31 | 4.34 | 4.33 | 4.33 | 4.29 | 4.27 | 4.28 | 4.22 | 4.2 | 4.23 |

[A] Sep. = Phase Separation;
[B] Aging Condition: −30° C. Freeze-Thaw; 3 Cycles
[C] Aging Condition: −10° C. Freeze-Thaw; 3 Cycles

TABLE 3

| | | | | | | | | | | |
|---|---|---|---|---|---|---|---|---|---|---|
| Viscosity (cP) of Control and Test Personal Care Compositions (C) and (1)-(17) [A] | | | | | | | | | | |
| # | Initial | −30° C. [B] F-T (×3) | −10° C. [C] F-T (×3) | 49° C. 4 wks | 30° C. 4 wks | 30° C. 8 wks | 30° C. 13 wks | 40° C. 4 wks | 40° C. 8 wks | 40° C. 13 wks |
| 1 | 22200 | 83600 | 95900 | Sep. | 20700 | 22500 | 48600 | 17700 | 19900 | 25400 |
| 2 | 49300 | 73800 | 82400 | Sep. | 37300 | 62200 | 94400 | 23100 | 29500 | 41800 |
| 3 | 25700 | 96300 | 89500 | 20000 | 30200 | 23600 | 50500 | 21600 | 24800 | 34800 |
| 4 | 34800 | Sep. | 77000 | 20800 | 27000 | 31900 | 45200 | 23600 | 26400 | 31800 |
| 5 | 65500 | 96200 | 95900 | Sep. | 57400 | 68500 | 105000 | 42300 | 45100 | 73200 |
| 6 | 43600 | Sep. | 77200 | Sep. | 35500 | 38800 | 56600 | 21800 | 23600 | 29200 |
| 7 | 16000 | Sep. | Sep. | Sep. | 13100 | 13500 | 19000 | Sep. | Sep. | Sep. |
| 8 | 14200 | Sep. | 63800 | Sep. | 12800 | 15500 | 24200 | 10800 | 12900 | 18800 |
| 9 | 53600 | 85600 | 86700 | Sep. | 57400 | 63500 | 103000 | 41100 | 42500 | 75800 |
| 10 | 38300 | 69100 | 54000 | Sep. | 32400 | 39600 | 63200 | 28600 | 26700 | 42600 |
| 11 | 88600 | 77500 | 95900 | 47300 | 85900 | 69100 | 126000 | 62700 | 64900 | 98400 |
| 12 | 24700 | 73800 | 62800 | Sep. | 20900 | 17800 | 32000 | 16100 | 14600 | 17000 |
| 13 | 74800 | 60500 | 72700 | Sep. | 65700 | 67800 | 115000 | 44200 | 44400 | 64200 |
| 14 | 31100 | Sep. | 80100 | Sep. | 24700 | 38900 | 59200 | 15900 | 17000 | 22000 |
| 15 | 44600 | 61800 | 53700 | Sep. | 33400 | 37600 | 59000 | 30300 | 28300 | 41600 |
| 16 | 53700 | 80800 | 90900 | Sep. | 52100 | 64400 | 106000 | 32100 | 32500 | 47400 |
| 17 | 40800 | 96400 | 96300 | 34600 | 42000 | 50400 | 77000 | 35400 | 37800 | 56400 |

[A] Sep. = Phase Separation;
[B] Aging Condition: −30° C. Freeze-Thaw; 3 Cycles
[C] Aging Condition: −10° C. Freeze-Thaw; 3 Cycles As illustrated in Tables 2 and 3, personal care compositions (3), (11), and (17) remained stable by maintaining acceptable pH and viscosity values, and did not exhibit any phase separation throughout the various accelerated aging conditions. It was observed that the physical properties of the personal care compositions (3), (11), and (17) were also unchanged throughout the various accelerated aging conditions. Particularly, the color, odor, and appearance of the personal care compositions (3), (11), and (17) were unchanged throughout the various accelerated aging conditions.

It should be appreciated that personal care compositions (3), (11), and (17) all contained cetearyl alcohol and ceteareth-20 at about 4% and cetyl alcohol at about 3.5%.

As indicated above, personal care compositions (3) included stearyl alcohol in an amount of about 3%, which resulted in a combined total fatty alcohol content of cetyl alcohol and stearyl alcohol to be about 6.5%. Personal care composition (3) also included isopropyl palmitate in an amount of about 1.5%.

Personal care composition (11) included stearyl alcohol in an amount of about 1.5%, cetyl alcohol in an amount of about 3.5%, thereby providing a total of the fatty alcohols of about 5%. Personal care composition (11) also included isopropyl palmitate in an amount of about 1.5%.

Personal care composition (17) included stearyl alcohol in an amount of about 3%, cetyl alcohol in an amount of about 3.5%, thereby providing a total of the fatty alcohols of about 6.5%. Personal care composition (11) also included isopropyl palmitate in an amount of about 1.5%.

It was surprisingly found that personal care composition (17) was the only stable personal care composition including isopropyl palmitate in an amount of about 4%.

It was surprisingly and unexpectedly discovered that stable personal care compositions having a pH of from about 4 to about 5 may be prepared when the primary emulsifier(s), namely, cetearyl alcohol and ceteareth-20, are present in an amount of about 4%, the combined amount of cetyl alcohol and stearyl alcohol is present in an amount of greater than or equal to about 5%, and cetyl alcohol is present in an amount of 3.5% or greater. It was also surprisingly and unexpectedly discovered that stable personal care compositions having a pH of from about 4 to about 5 may be prepared when the isopropyl palmitate is present in an amount of about or at least 1.5%. It was further surprisingly and unexpectedly discovered that if isopropyl palmitate is present in an amount of about 4%, then stable personal care compositions having a pH of from about 4 to about 5 may be prepared by providing a total of cetyl alcohol and stearyl alcohol of about 6.5% or greater, and/or an amount of cetearyl alcohol/ceteareth-20 in an amount of about 4% or greater.

Example 3

The whiteness, absorbability, spreadability, tackiness, and greasiness were also evaluate. To evaluate whiteness, absorbability, tackiness, spreadability, and greasiness, a Small Sensory Panel of ten panelists for sensory properties was utilized. Each of the ten panelists assessed each of the test personal care compositions (3), (11), and (17) by using a standardized methodology and a 0 to 5 point assessment scale, where '0' represented the lowest level (i.e., none or low) and '5' represented the highest value. A controlled amount of each of the test personal care compositions (3), (11), and (17) was applied for the analysis. The results analyzing the sensory properties of personal care compositions (3), (11), and (17) are summarized in Table 4.

TABLE 4

Sensory Properties of Personal Care Compositions (3), (11), and (17)

| Composition | W | Std Dev | A[C] | Std Dev | T[C] | Std Dev | S[C] | Std Dev | G[C] | Std Dev |
|---|---|---|---|---|---|---|---|---|---|---|
| (3) | 2.00 | 1.41 | 3.70 | 1.16 | 2.00 | 1.15 | 4.20 | 0.79 | 2.00 | 1.05 |
| (11) | 2.00 | 1.49 | 3.90 | 0.74 | 2.50 | 1.27 | 4.10 | 0.57 | 2.00 | 1.25 |
| (17) | 1.70 | 0.95 | 3.90 | 0.88 | 1.70 | 0.67 | 4.00 | 0.94 | 2.00 | 1.15 |

[C] W = Whiteness; A = Absorbability; S = Spreadability; T = Tackiness; G = Greasiness The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A personal care composition, comprising:
   an emulsifying system comprising 0.1-2 weight % of cationic surfactants and 2-5 weight % of nonionic surfactants;
   fatty alcohols comprising cetyl alcohol, stearyl alcohol, or combinations thereof, wherein the cetyl alcohol and the stearyl alcohol are present in an amount of greater than or equal to 5 weight %, based on a total weight of the personal care composition;
   0.1-5 weight % of one or more emollients; and
   1-6 weight % of one or more humectants; all based on a total weight of the personal care composition;
   wherein the nonionic surfactants comprises cetearyl alcohol, ceteareth-20, or combinations thereof, and wherein cetearyl alcohol and/or ceteareth-20 are present in an amount of 3 weight % to 5 weight %, based on a total weight of the personal care composition;
   wherein the personal care composition has an acidic pH of from 4.2 to 4.8; and
   wherein the personal care composition is selected from the group consisting of:
   (A) a formulation comprising 0.03 weight % of Dipalmitoylethel Dimonium Chloride, 4.00 weight % of Cetearyl Alcohol/Ceteareth-20, 3.00 weight % of Stearyl Alcohol, 3.50 weight % of Cetyl Alcohol, and 1.50 weight % of Isopropyl Palmitate, based on the total weight of the personal care composition;
   (B) a formulation comprising 0.50 weight % of Dipalmitoylethyl Dimonium Chloride, 4.00 weight % of Cetearyl Alcohol/Ceteareth-20 1.50 weight % of Stearyl Alcohol, 3.50 weight % of Cetyl Alcohol, and 1.50 weight % of Isopropyl Palmitate, based on the total weight of the personal care composition; and
   (C) a formulation comprising 0.05 weight % of Dipalmitoylethyl Dimonium Chloride, 4.00 weight % of Cetearyl Alcohol/Ceteareth-20, 3.00 weight % of Stearyl Alcohol, 3.50 weight % of Cetyl Alcohol, and 4.00 weight % of Isopropyl Palmitate, based on the total weight of the personal care composition.

2. The personal care composition of claim 1, wherein the cationic surfactant further comprises an esterquat.

3. The personal care composition of claim 1, wherein the one or more humectants comprise glycerin, caprylyl glycol, or combinations thereof.

4. The personal care composition of claim 1, wherein the personal care composition is substantially free of silicone, silicone compounds, propylene glycol, mineral oil, petrolatum, polyethylene glycol (PEG), or any combination thereof.

5. The personal care composition of claim 1, wherein the personal care composition is substantially free of silicone, silicone compounds, propylene glycol, mineral oil, petrolatum, or any combination thereof.

6. The personal care composition of claim 1, further comprising one or more acids, wherein the acids comprise lactic acid.

7. The personal care composition of claim 1, wherein the personal care composition has an acidic pH of from 4.2 to 4.6.

8. The personal care composition of claim 1, wherein the personal care composition has a viscosity of greater than or equal to 50,000 centipoise (cP) and less than or equal to 200,000 cP at 25° C.

9. The personal care composition of claim 1, wherein the personal care composition does not exhibit phase separation after exposure to accelerated aging conditions.

10. A method for preparing the personal care composition of claim 1, the method comprising contacting the emulsifying system, the fatty alcohols, the one or more emollients, and the one or more humectants with one another.

* * * * *